United States Patent [19]

Krasnobajew et al.

[11] 4,184,986

[45] Jan. 22, 1980

[54] NOVEL CONDENSATION PRODUCTS HAVING HIGH ACTIVITY TO INSOLUBILIZE PROTEINS AND PROTEIN-INSOLUBILIZED PRODUCTS

[75] Inventors: Victor Krasnobajew, Zollikerberg; Regula Böeniger, Greifensee, both of Switzerland

[73] Assignee: Givaudan Corporation, Clifton, N.J.

[21] Appl. No.: 821,663

[22] Filed: Aug. 3, 1977

Related U.S. Application Data

[62] Division of Ser. No. 605,965, Sep. 19, 1975, abandoned.

[51] Int. Cl.$^2$ .................... C08L 61/20; C08L 61/32; C12K 1/00
[52] U.S. Cl. ........................ 260/6; 106/124; 435/180; 260/112 R
[58] Field of Search ............ 106/124, 125; 260/6, 260/2.1 C; 195/63

[56] References Cited

U.S. PATENT DOCUMENTS

| | | | |
|---|---|---|---|
| 2,645,627 | 7/1953 | Gustus | 260/2.1 C |
| 2,671,059 | 3/1954 | Smit | 260/2.1 C |
| 3,660,317 | 5/1972 | Masatsugu | 260/2.1 C |

OTHER PUBLICATIONS

"Reaction of Collagen-Cross-linking Aldehydes with Phenylenediamine" Nature, vol. 205, 3-13-65, pp. 1108-1110.

*Primary Examiner*—Theodore Morris
*Attorney, Agent, or Firm*—Thomas Cifelli, Jr.; Robert F. Tavares

[57] ABSTRACT

The novel condensation product of 1,3-phenylenediamine and glutardialdehyde has high activity to fix or insolubilize proteins, including enzymers.

1 Claim, No Drawings

NOVEL CONDENSATION PRODUCTS HAVING HIGH ACTIVITY TO INSOLUBILIZE PROTEINS AND PROTEIN-INSOLUBILIZED PRODUCTS

This is a division of application Ser. No. 605,965 filed Aug. 19, 1975 now abandoned.

FIELD OF THE INVENTION

This invention relates to the field of insolubilizing proteins.

RELATED APPLICATIONS

This application is related to pending U.S. Pat. applications, Ser. No. 440,438, filed Feb. 7, 1974 and Ser. No. 571,187, filed Apr. 24, 1975. The latter application is a divisional application of Ser. No. 440,438. This application is also related to Ser. No. 593,605, filed July 7, 1975 all now abandoned.

The relationship of this application to the first two aforesaid applications is that this is a continuation-in-part application of the first two applications mentioned. A clear line of distinction exists as to the claims in all three applications.

PRIOR ART

The manufacture of a condensation resin having a large bonding capacity for proteins, by the reaction of 1,3-phenylenediamine and formaldehyde, as well as diazotisation of the reaction product, is known.

It has suprisingly been found, in accordance with the present invention, that a substantially more active product with respect to the fixing or insolubilizing of proteins is obtained when the novel condensation products of the present invention are used as carriers for the proteins.

SUMMARY OF THE INVENTION

It is known that proteins, especially enzymes, can be bonded to solid carrier materials to give insoluble products which have advantageous properties. The bonded, insolubilized, but biologically active, proteins can, for example, be more readily handled than in their naturally soluble form. Because they can be readily recovered, enzymes bonded to a carrier can be used several times in a stationary process or, with particular advantage, in a process which is continuously worked.

Thus, for example, the manufacture of a condensation resin having a large bonding capacity for proteins by the reaction of 1,3-phenylenediamine and formaldehyde as well as the diazotisation of the reaction product are known.

It has now surprisingly been found in accordance with the present invention that a substantially more active product with respect to the fixing or insolubilizing of proteins is obtained when 1,3-phenylenediamine is condensed with glutardialdehyde.

The present invention is based on the foregoing finding and is accordingly concerned with a novel condensation product manufactured by the condensation of 1,3-phenylenediamine with glutardialdehyde.

As compared with the aforementioned known condensation product manufactured from 1,3-phenylenediamine and formaldehyde, the novel condensation product manufactured from 1,3-phenylenediamine and glutardialdehyde has a number of very advantageous properties which make it excellently suitable as a carrier material for the fixing of proteins of the most diverse type and origin: it forms larger particles which are easier to filter (i.e., free flow is guaranteed when the material is placed on a G-1 to G-4 sintered glass disc. No suction or pressure is required), quicker to sediment and therefore generally better to handle; the bonding capacity for proteins is substantially greater; the novel consideration product is already an activated carrier which can be used immediately and can bring about the fixing of the protein in a very simple manner because of the high activity. Finally, the condensation product of this invention is very inexpensive.

The invention is also concerned with a process for the manufacture of the aforementioned novel condensation product, namely 1,3-phenylenediamine glutardialdehyde resin (PAG-resin), which process comprises reacting 1,3-phenylenediamine with glutardialdehyde. The invention is further concerned with a process for the fixing of proteins to the PAG-resin and with the proteins fixed to the PAG-resin.

DESCRIPTION OF THE PREFERRED EMBODIMENTS

Proteins which can be bonded to the condensation products in accordance with the present invention include polypeptides, antigens, antibodies, protein inhibitors and, especially, enzymes. The enzymes can be of vegetables, animal or microbial origin. The enzymes may be hydrolases (Peptidases, proteinases, desaminases, carbohydrases, nucleases), lyases or desmolases (hydrolyases, decarboxylases, aldolases), transferases, isomerases, oxidoreductases, and ligases. Examples of enzymes from which insoluble enzyme preparations provided by this invention can be manufactured are alcoholdehydrogenase, naringinase, hesperidinase, $\beta$-glucosidase, $\alpha$-amylase, invertase, amyloglucosidase, urease trypsin, ficin, papain, bromelin, subtilopeptidase, rennin, glucoseisomerase, glucoseoxidase, peroxidase, catalase, acylase, cytochrome, ribonuclease, phosphodiesterase and adenyldeaminase.

The molar ratio of the polyamine and aldehyde reaction products expediently lies at between 1:1 and 1:10, a ratio of about 1:3 being preferred.

The reaction can be carried out in a manner known per se; for example, in aqueous solution, preferably with the addition of an acid such as a mineral acid (e.g., hydrochloric acid). In a particular embodiment, the reaction is carried out in the presence of an inert, fine-grained, preferably inorganic, especially silicate-containing, adjuvant. Examples of such adjuvants are silica gel, pumice-stone, diatomaceous earth (kieselguhr), bentonite, wollastonite, porous glass and also metal oxides such as aluminum oxide or hydroxylapatite. It is preferred to use silica gel (e.g., with a particle size of 0.05–0.2 mm, 70–325 mesh) or pumice stone (e.g., with a paricle size of 0.05–10 mm). The presence of such an adjuvant gives rise to a homogeneous particle formation in the reaction and, as a result an improved sedimentation is achieved. The reaction in the presence of an adjuvant is expediently carried out by initially bringing the particles into contact with one of the two reaction components and then adding the second component with simultaneous or subsequent slight acidification.

The reaction can be carried out in a homogeneous phase or, preferably, in a two-phase system with the addition of an acid such as a mineral acid (e.g. sulphuric acid, phosphoric acid or, preferably, hydrochloric acid) or an organic acid (e.g., a carboxylic acid such as acetic acid) with vigorous stirring or shaking. The use of a two-phase system promotes the formation of spherical, substantially homogeneous particles which are easy to filter and which sedment well, these particles being especially well suited as a carrier material. The reaction products are amorphous materials which are insoluble in water and the usual organic solvents. The exact structure of the polymer is not known, however, quinoline, 1,7-phenanthroline and 1,6-diazaphenalene units are present in the molecules.

Inert, water-immiscible organic solvents (e.g., dichloromethane, chloroform, carbon tetrachloride, benzene, toluene, ethyl acetate, dioxane, carbon disulphide) are suitable as the second phase. Chloroform is preferably used as the inert, water-immiscible solvent, but acetone is also suitable for this purpose.

The reaction temperature is not critical; it can lie, for example, at between 0° C. and 50° C., preferably at room temperature (i.e., at about 18°-22° C.).

In accordance with the process provided by this invention there is obtained a condensation product carrier material which, although already very active, can be still further activated by diazotisation. The diazotisation can be carried out in a manner known per se by treatment with nitrite and acid.

In order to fix the protein to the carrier masterial, the latter is treated with an aqueous solution, preferably a buffered solution, of the protein (1–50 mg/ml) at a temperature of 0°-30° C., preferably 4° C. to room temperature. This treatment can be carried out while stirring or shaking. Because of the high activity of the carrier material, the fixing of the proteins can also be advantageously carried out by simply filtering the protein solution through a carrier layer, preferably a column filled with the carrier material as is common, for example, in column chromatography. Thus, for example, culture filtrates of microorganisms which contain proteins or enzymes can be allowed to run directly through a column of carrier material, the proteins or enzymes being selectively fixed to the carrier. The column is expediently rinsed with a buffer solution and 1-M potassium chloride solution in order to remove the non-fixed proteins.

The proteins fixed to the carrier material are generally very stable and very high specific activities (unit/g) are achieved in the case of enzymes. Loadings of, for example, 1:30-10 parts by weight of protein/carrier material are achieved.

The carrier-bonded proteins provided by this invention, especially enzymes, can be used in a manner known per se; for example, for analytical or preparative purposes or in food technology such as in the manufacture of glucose from starch [see, for example, *Scientific American* 224, (No. 3) 26 –33 (1971); *Angew, Chemie* 84, (8) 319-268 (1972); *Chemiker Zeitung* 96, (11), 595-602 (1972); *C & EN*, (15.2.71), 86-87].

In this important large-scale process, amyloglucosidase fixed to the condensation product provided by the present invention can be utilised for the manufacture of glucose from the "glucose syrup" (prehydrolysed starch). The condensation products can then be transferred, for example, onto columns (fixed-bed process). A further application results in the enzymatic degradation of lactose in milk products by means of lactases (e.g., "sweets" from whey).

The following Examples illustrate the present invention. The quantative data of the carrier material obtained or used is given with respect to dry weight.

EXAMPLE 1

50 g of glutardialdehyde (25% aqueous solution) were added with vigorous stirring to a solution of 5.0 of 1,3-phenylenediamine in 50 ml of water and 10 ml of concentrated hydrochloric acid. When solidification of the reaction mixture occurred, 300 ml of water were added. The mixture was stirred for a further hour at room temperature and then evaporated under reduced pressure via a Büchner funnel. The fine polymeric particles were washed with 0.1-N sodium hydroxide and water and stored in 0.01-N sodium hydroxide. The yield amounted to 13.8 g.

EXAMPLE 2

50 g of glutardialdehyde were added with vigorous stirring to a solution of 5 g of 1,3-phenylenediamine in 300 ml of chloroform and, after a further 5 minutes, 20 ml of 7-N hydrochloric acid were added. The reaction mixture solidified immediately. It was treated with 100 ml of water and shaken for 5 minutes until it again became liquid. After filtration of the mixture under a vacuum via a Büchner funnel, the polymeric particles were washed with 0.1-N sodium hydroxide. The residual chloroform was removed by washing with acetone. The yield amounted to 14 g. The thus-obtained carrier particles were spherical, homogeneous and capable of good filtration. They were stored in water or in dilute sodium hydroxide.

EXAMPLE 3

30 g of silica gel were added with stirring to a solution of 2.0 g of 1,3-phenylenediamine in 50 ml of benzene. After stirring for 10 minutes at room temperature, the silica gel was filtered off via a Büchner funnel and sucked dry. Benzene still adhering to the silica gel did not interfere with the further reaction. The silica gel particles impregnated with 1,3-phenylenediamine were then rapidly added with vigorous stirring to a mixture of 50 g of glutardialdehyde (25% solution in water), 10 ml of concentrated hydrochloric acid and 340 ml of water. Polymerisation occurred immediately. The orange-red polymer was stirred for 1 hour at room temperature, filtered off under reduced pressure via a Büchner funnel and washed with water until neutral. The thus-obtained carrier material was then stored in a weakly alkaline solution (0.01-N sodium hydroxide).

EXAMPLE 4

30 g of silica gel were added with vigorous stirring to 50 g of glutardialdehyde (25% aqueous solution). The mass was then added with vigorous shaking to a solution of 5 g of 1,3-phenylenediamine in 300 ml of chloroform. After the addition of 10 ml of 7-N hydrochloric acid and 100 ml of water, the mixture was shaken for a further 10 minutes. The product was worked up in the same manner as described in Example 2. There were obtained homogeneous, spherical particles which sedimented quickly and which could be filtered in an excellent manner.

EXAMPLE 5

Carrier mateials were manufactured in a manner analogous to that described in Example 3 and Example 4 using diatomaceous earth in place of silica gel.

EXAMPLE 6

A suspension of 1 of the condensation product obtained according to Examples 1–5 in 30 ml of waste was acidified with 1.15 ml of concentrated hydrochloric acid at 0° C. A 1-N sodium nitrite solution was added dropwise, with stirring, to the ice-cold suspension. At the end of the diazotisation, the black-violet coloured carrier material was filtered off, washed with cold water and a buffer solution (pH 4–8.5, depending on the pH value of the protein solution which is subsequently to be fixed to the carrier material).

EXAMPLE 7

0.23 g of the carrier material obtained according to Example 2 were diazotised in the manner described in Example 6 and filled into a chromatography column (1.5×15 cm). A solution of 1 g of amylglucosidase (52 units/mg) in 100 ml of 16 mmol acetate buffer (pH 4.8) was passed through the column at room temperature and with a flow rate of 20 ml per hour. The fixed enzyme had an activity of 7,000 units/g of carrier material.

EXAMPLE 8

A suspension of 1 g of diazotised carrier material (obtained according to Example 3 or Example 4) in 20 mmol of phosphate buffere (pH 5.2) was filled into a chromatography column (1.5×15 cm). A solution of 500 mg of invertase (150 units/mg) in 50 ml of 20 mmol phosphate buffer (pH 5.2) was passed through the column at room temperature and with a flow rate of 20 ml per hour. The column was washed with 50 ml of 20 mmol phosphate buffer (pH 5.2) and 50 ml of 1-N potassium chloride solution. The amount of fixed enzyme was 349 mg. The activity of the fixed enzyme was 4,280 units/g of carrier material. The activity of the bonded enzymes was 8.5% compared with the soluble enzyme. The weight ratio of enzyme to carrier material was about 1:3. An invertase preparation manufactured in an analogous manner from 20 g of diazotised carrier material showed an activity of 17.6% compared with that of the soluble enzyme.

EXAMPLE 9

1 g of diazotised carrier material (manufactured according to Example 3 or Example 4) in 0.1-M phosphate buffer (pH 7.0) was filled into a chromatography column (1.5×15 cm). A solution of 600 mg of ficin in 60 ml of a solution of 0.1-M phosphate buffer, 7 mmol of mercaptoethanol and 1 mmol of EDTA (pH 7.0) was passed through the column at room temperature and with a flow rate of 20 ml per hour. The column was rinsed with 50 ml of the same buffer solution and 50 ml of 1-M potassium chloride solution. The amount of fixed enzyme was 459 mg. The activity of the fixed enzyme determined with casein as the substrate amounted to 15% of the activity of the soluble enzyme.

EXAMPLE 10

A solution of 4 g of naringinase in 100 ml of 0.05-M citrate buffer (pH 6.5) was passed at room temperature and with a flow rate of 20 ml per hour through a column containing 2 g of diazotised carrier material obtained according to Example 3 or Example 4. The carrier-bonded maringinase showed an activity of 32% compared with the soluble enzyme.

EXAMPLE 11

2 g of diazotised carrier material obtained according to Example 3 or Example 4 were shaken for 1 hour at 4° C. with a solution of 600 mg of naringinase in 50 ml of 0.05-M citrate buffer (pH 6.5). The activity of the fixed naringinase amounted to 50% campared with that of the soluble enzyme.

EXAMPLE 12

In an analogous manner as described in Example 11, 40 mg of hesperidinase in 50 ml of 0.05-M citrate buffer (pH 6.5) were bonded to the carrier material. The activity of the fixed enzyme amounted to 27% of that of the soluble enzyme.

EXAMPLE 3

A solution of unpurified glucose-isomerase, obtained from the partially purified culture filtrate of a microorganism (*Streptomyces glaucescens*), was passed through a column containing 50 g of diazotised carrier material manufactured according to Example 3 or Example 4. The column was washed with 0.05-H phosphate buffer (pH 6.5) and 1-M potassium chloride solution. The activity of the fixed glucose-isomerase amounted to 74% of that the soluble enzyme, determined by measuring the isomerization of a 10% glucose solution to fructose.

EXAMPLE 14

A solution of 100 mg of bovine serum albumin in 50 ml of 0.05-M phosphate buffer (pH 6.5) was passed through a chromatography column (1.5×5 cm) containing 0.5 g of diazotised carrier material, obtained according to Example 3 or Example 4, at room temperature and at a flow rate of 20 ml per hour. 68.4 mg of the albumin was bonded to the carrier so that the weight ratio of bonded protein to carrier material amounted to about 1.4:10.

Approximately the same coupling ratio was obtained when a non-diazotised carrier material was used.

What we claim is:

1. A protein bonded to the condensation product obtained by reacting 1,3-phenylene-diamine with glutardialdehyde, said product comprising spherical, homogeneous particles capable of good filtration.

* * * * *